(12) United States Patent
Adams et al.

(10) Patent No.: US 11,860,077 B2
(45) Date of Patent: Jan. 2, 2024

(54) FLUID FLOW SENSOR USING DRIVER AND REFERENCE ELECTROMECHANICAL RESONATORS

(71) Applicant: Saudi Arabian Oil Company, Dhahran (SA)

(72) Inventors: Robert Adams, Houston, TX (US);
Edwin Hulse, Houston, TX (US);
Miguel Gonzalez, Houston, TX (US);
Tim Thiel, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 76 days.

(21) Appl. No.: 17/551,031

(22) Filed: Dec. 14, 2021

(65) Prior Publication Data

US 2023/0184655 A1 Jun. 15, 2023

(51) Int. Cl.
*G01N 11/16* (2006.01)
*E21B 49/08* (2006.01)

(52) U.S. Cl.
CPC .......... *G01N 11/16* (2013.01); *E21B 49/0875* (2020.05)

(58) Field of Classification Search
CPC ...... E21B 49/0875; G01N 11/00; G01N 11/16
See application file for complete search history.

(56) References Cited

U.S. PATENT DOCUMENTS 2,558,427 A 6/1951 Fagan
3,885,212 A 5/1975 Herbert
(Continued)

FOREIGN PATENT DOCUMENTS

CN 103441803 12/2013
CN 103701567 4/2014
(Continued)

OTHER PUBLICATIONS

M. Gonzalez et al., "Electromechanical Tuning Fork Resonator For Drilling Fluid Viscometry and Densitometry," 2019 IEEE SENSORS, Montreal, QC, Canada, 2019, pp. 1-4, doi: 10.1109/SENSORS43011.2019.8956900. (Year: 2019).*
(Continued)

*Primary Examiner* — John Fitzgerald
(74) *Attorney, Agent, or Firm* — Fish & Richardson P.C.

(57) ABSTRACT

Systems and methods include a computer-implemented method for performing real-time measurements of drilling fluid in a well. A driver and a reference are monitored for responses by a measurement controller of a system for measuring fluid flow. The driver is configured as a driving electromechanical resonator for contacting the drilling fluid. The reference is configured as a reference electromechanical resonator for contacting the drilling fluid. The reference is of a similar construction as the driver and is in contact with the drilling fluid in a substantially same way. Real-time measurements are performed by the measurement controller based on information received from the driver and reference. A viscosity and density of the drilling fluid are determined based on the real-time measurements. The similar construction of the driver and reference enables mitigation of environmental sensitivities of the driver and reference, enhancing fluid property sensitivities to physical properties of the drilling fluid.

20 Claims, 4 Drawing Sheets

(56) References Cited

U.S. PATENT DOCUMENTS

| | | | |
|---|---|---|---|
| 4,023,092 A | 5/1977 | Rogers | |
| 4,331,025 A | 5/1982 | Ord, Jr. | |
| 4,589,285 A | 5/1986 | Savit | |
| 4,650,281 A | 3/1987 | Jaeger et al. | |
| 4,754,640 A | 7/1988 | Fitzgerald et al. | |
| 4,808,925 A | 2/1989 | Baird | |
| 4,983,912 A | 1/1991 | Roehrlein | |
| 5,040,415 A * | 8/1991 | Barkhoudarian | G01P 5/24 73/861.03 |
| 5,096,277 A | 3/1992 | Kleinerman | |
| 5,158,440 A | 10/1992 | Cooper et al. | |
| 5,177,997 A | 1/1993 | Maciejewski | |
| 5,271,267 A * | 12/1993 | Baumoel | G01N 9/002 73/32 A |
| 5,335,542 A | 8/1994 | Ramakrishnan et al. | |
| 5,365,778 A * | 11/1994 | Sheen | G01N 29/024 73/32 A |
| 5,387,863 A | 2/1995 | Lo | |
| 5,494,413 A | 2/1996 | Campen et al. | |
| 5,649,811 A | 7/1997 | Krol, Jr. et al. | |
| 5,729,607 A | 3/1998 | DeFries et al. | |
| 5,767,668 A | 6/1998 | Durand | |
| 6,250,848 B1 | 6/2001 | Moridis et al. | |
| 6,380,534 B1 | 4/2002 | Mahmoud et al. | |
| 6,411,084 B1 | 6/2002 | Yoo | |
| 6,555,807 B2 | 4/2003 | Clayton et al. | |
| 6,808,371 B2 | 10/2004 | Niwatsukino et al. | |
| 6,811,382 B2 | 11/2004 | Buchanan et al. | |
| 6,853,200 B2 | 2/2005 | Munser | |
| 6,854,338 B2 * | 2/2005 | Khuri-Yakub | G01F 1/667 73/861.27 |
| 6,856,132 B2 | 2/2005 | Appel et al. | |
| 7,021,905 B2 | 4/2006 | Torrey et al. | |
| 7,520,162 B2 | 4/2009 | Wenger et al. | |
| 7,622,915 B2 | 11/2009 | Sugiyama | |
| 7,831,205 B2 | 11/2010 | Jack et al. | |
| 7,898,494 B2 | 3/2011 | Brune | |
| 8,141,434 B2 | 3/2012 | Kippersund et al. | |
| 8,229,699 B2 | 7/2012 | Jin | |
| 8,269,501 B2 | 9/2012 | Schmidt et al. | |
| 8,272,455 B2 | 9/2012 | Guimerans | |
| 8,638,104 B2 | 1/2014 | Barber et al. | |
| 8,661,907 B2 | 3/2014 | Davis et al. | |
| 8,816,689 B2 | 8/2014 | Colombo et al. | |
| 8,877,954 B2 | 11/2014 | Giesenberg et al. | |
| 8,885,559 B2 | 11/2014 | Schmidt et al. | |
| 9,051,829 B2 | 6/2015 | Xie | |
| 9,080,097 B2 | 7/2015 | Gupta et al. | |
| 9,129,728 B2 | 9/2015 | Edbury | |
| 9,133,709 B2 | 9/2015 | Huh et al. | |
| 9,528,322 B2 | 12/2016 | MacDonald | |
| 10,117,042 B2 | 10/2018 | Akyildiz et al. | |
| 10,273,399 B2 | 4/2019 | Cox et al. | |
| 10,308,865 B2 | 6/2019 | Cox et al. | |
| 10,308,895 B2 | 6/2019 | Vidal et al. | |
| 10,317,557 B2 | 6/2019 | Gonzalez et al. | |
| 10,323,644 B1 | 6/2019 | Shakirov et al. | |
| 10,349,249 B2 | 7/2019 | Akyildiz et al. | |
| 10,444,065 B2 | 10/2019 | Schmidt et al. | |
| 10,487,259 B2 | 11/2019 | Cox et al. | |
| 10,501,682 B2 | 12/2019 | Cox et al. | |
| 11,061,158 B2 | 7/2021 | Gonzalez et al. | |
| 11,333,015 B2 * | 5/2022 | Seren | H03F 3/45475 |
| 11,549,345 B2 * | 1/2023 | Lakhamraju | E21B 43/12 |
| 2002/0173922 A1 * | 11/2002 | Potyrailo | G01N 29/036 702/39 |
| 2003/0220204 A1 | 11/2003 | Baran et al. | |
| 2004/0006436 A1 * | 1/2004 | Morgen | G01F 1/663 702/48 |
| 2004/0236512 A1 | 11/2004 | DiFoggio et al. | |
| 2005/0152280 A1 | 7/2005 | Pollin | |
| 2006/0076956 A1 | 4/2006 | Sjolie et al. | |
| 2006/0105052 A1 | 5/2006 | Acar et al. | |
| 2007/0114030 A1 | 5/2007 | Todd et al. | |
| 2008/0290876 A1 | 11/2008 | Ameen | |
| 2009/0093977 A1 * | 4/2009 | Hauptmann | G01F 1/66 702/54 |
| 2009/0222921 A1 | 9/2009 | Mukhopadhyay et al. | |
| 2009/0255669 A1 | 10/2009 | Ayan et al. | |
| 2009/0264067 A1 | 10/2009 | Pahlavan | |
| 2009/0264768 A1 | 10/2009 | Courtney | |
| 2009/0277625 A1 | 11/2009 | Bai et al. | |
| 2009/0289627 A1 | 11/2009 | Johansen et al. | |
| 2010/0191110 A1 | 7/2010 | Insana et al. | |
| 2010/0200744 A1 | 8/2010 | Pearce et al. | |
| 2010/0227557 A1 | 9/2010 | Won et al. | |
| 2010/0241407 A1 | 9/2010 | Hsu et al. | |
| 2011/0030949 A1 | 2/2011 | Weaver et al. | |
| 2011/0271769 A1 * | 11/2011 | Kippersund | G01F 1/86 73/861.28 |
| 2012/0055263 A1 * | 3/2012 | Konzelmann | G01F 1/34 73/861.18 |
| 2012/0092960 A1 | 4/2012 | Gaston et al. | |
| 2012/0135080 A1 | 5/2012 | Bromberg et al. | |
| 2012/0281643 A1 | 11/2012 | Sun | |
| 2013/0043887 A1 | 2/2013 | Ziolkowski et al. | |
| 2013/0073208 A1 | 3/2013 | Dorovsky | |
| 2013/0091292 A1 | 4/2013 | Kim et al. | |
| 2013/0109261 A1 | 5/2013 | Koene | |
| 2013/0192349 A1 | 8/2013 | Ramkumar et al. | |
| 2013/0244914 A1 | 9/2013 | Wu et al. | |
| 2013/0250812 A1 | 9/2013 | Rath | |
| 2013/0296453 A1 | 11/2013 | Giesenberg et al. | |
| 2013/0312970 A1 | 11/2013 | Lafitte et al. | |
| 2013/0332015 A1 | 12/2013 | Dextreit et al. | |
| 2013/0341030 A1 | 12/2013 | Brannon et al. | |
| 2014/0036628 A1 | 2/2014 | Hill et al. | |
| 2014/0041862 A1 | 2/2014 | Ersoz | |
| 2014/0060832 A1 | 3/2014 | Mahoney et al. | |
| 2014/0133276 A1 | 5/2014 | Volker | |
| 2014/0159715 A1 | 6/2014 | McEwen-King | |
| 2014/0190700 A1 | 7/2014 | Tang et al. | |
| 2014/0200511 A1 | 7/2014 | Boyden | |
| 2014/0366069 A1 | 12/2014 | Ramamurthi | |
| 2015/0000657 A1 | 1/2015 | Varvello et al. | |
| 2015/0013983 A1 | 1/2015 | Alwattari | |
| 2015/0036482 A1 | 2/2015 | Schmidt et al. | |
| 2015/0050741 A1 | 2/2015 | Tour et al. | |
| 2015/0094964 A1 | 4/2015 | Kuroda et al. | |
| 2015/0118501 A1 | 4/2015 | Lu | |
| 2015/0159079 A1 | 6/2015 | Huh et al. | |
| 2015/0181315 A1 | 6/2015 | Vuran et al. | |
| 2015/0192436 A1 | 7/2015 | Farhadiroushan et al. | |
| 2015/0264627 A1 | 9/2015 | Perdomo et al. | |
| 2015/0268370 A1 | 9/2015 | Johnston et al. | |
| 2015/0319630 A1 | 11/2015 | Kerberg | |
| 2015/0337874 A1 | 11/2015 | Park | |
| 2015/0368547 A1 | 12/2015 | Lesko et al. | |
| 2015/0376493 A1 | 12/2015 | Huh et al. | |
| 2016/0040514 A1 | 2/2016 | Rahmani et al. | |
| 2016/0083641 A1 | 3/2016 | Gamage | |
| 2016/0138964 A1 | 5/2016 | Brengartner et al. | |
| 2016/0146662 A1 | 5/2016 | Stokely et al. | |
| 2016/0187172 A1 | 6/2016 | Gottlieb | |
| 2016/0264846 A1 | 9/2016 | Bennetzen et al. | |
| 2016/0305447 A1 | 10/2016 | Dreiss et al. | |
| 2017/0074093 A1 | 3/2017 | Adebayo | |
| 2017/0314976 A1 * | 11/2017 | Gottlieb | G01F 1/662 |
| 2018/0313735 A1 | 11/2018 | Gallagher | |
| 2018/0320059 A1 | 11/2018 | Cox et al. | |
| 2019/0226900 A1 | 7/2019 | Brengartner et al. | |
| 2019/0323338 A1 * | 10/2019 | Seren | E21B 47/06 |
| 2021/0041591 A1 | 2/2021 | Riachentsev | |
| 2021/0208046 A1 | 7/2021 | Gonzalez et al. | |

FOREIGN PATENT DOCUMENTS

| | | |
|---|---|---|
| DE | 4419684 | 12/1995 |
| EP | 1721603 | 11/2006 |
| EP | 2789793 | 10/2014 |
| EP | 2801696 | 11/2014 |
| GB | 2442745 | 4/2011 |
| RU | 2025747 | 12/1994 |

(56) References Cited

FOREIGN PATENT DOCUMENTS

| | | |
|---|---|---|
| WO | WO 1998046857 | 10/1998 |
| WO | WO 2000023824 | 4/2000 |
| WO | WO 2004113677 | 12/2004 |
| WO | WO 2011063023 | 5/2011 |
| WO | WO 2012154332 | 11/2012 |
| WO | WO 2012158478 | 11/2012 |
| WO | WO 2013142869 | 9/2013 |
| WO | WO 2014049698 | 4/2014 |
| WO | WO 2014066793 | 5/2014 |
| WO | WO 2014100275 | 6/2014 |
| WO | WO 2015020642 | 2/2015 |
| WO | WO 2015044446 | 4/2015 |
| WO | WO 2015084926 | 6/2015 |
| WO | WO 2015086062 | 6/2015 |
| WO | WO 2015095168 | 6/2015 |
| WO | WO 2015134705 | 9/2015 |
| WO | WO 2017205565 | 11/2017 |
| WO | WO 2018022198 | 2/2018 |

OTHER PUBLICATIONS

Agbinya, "A Magneto-Inductive Link Budget for Wireless Power Transfer and Inductive Communication Systems," Progress in Electromagnetics Research C, 37: 15-28, 2013, 14 pages.

Agbinya, "Investigation of Near Field Inductive Communication System Models, Channels and Experiments," Progress in Electromagnetics Research B, 49: 129-153, 2013, 25 pages.

Akinade et al., "Improving The Rheological Properties of Drilling Mud Using Local Based Materials", American Journal of Engineering Research., Jan. 2018, 7 pages.

Akyildiz et al., "SoftWater: Software-Defined Networking for Next-Generation Underwater Communication Systems," Ad Hoc Networks, 46: 1-11, Apr. 8, 2016, 11 pages.

Al-Hameedi et al., "Mud loss estimation using machine learning approach", Journal of Petroleum Exploration and Production Technology., Jun. 2019, 9(2): 1339-1354, 16 pages.

Alsaihati et al., "Real-Time Prediction of Equivalent Circulation Density for Horizontal Wells Using Intelligent Machines", ACS Omega., Jan. 2021, 6(1): 934-942, 9 pages.

americanpiezo.com [online], "Stripe Actuators," available on or before Mar. 13, 2011, via Internet Archive: Wayback Machine URL <https://web.archive.org/web/20110313073802/https://www.americanpiezo.com/standard-products/stripe-actuators.html>, [retrieved on Apr. 6, 2018], retrieved from: URL <https://www.americanpiezo.com/standard-products/stripe-actuators.html>, 2 pages.

Anoop et al. "Viscosity measurement dataset for a water-based drilling mud-carbon nanotube suspension at high-pressure and high-temperature", Data in Brief., Jun. 2019, 24: 103816, 5 pages.

Assaf et al., "Accurate Sensors Localization in Underground Mines or Tunnels," IEEE, 2015, 6 pages.

Bagaria et al., "Iron Oxide Nanoparticles Grafted with Sulfonated Copolymers are Stable in Concentrated Brine at Elevated Temperatures and Weakly Adsorb on Silica," ACS Applied Materials & Interfaces, 5:8 (3329-3339), Mar. 25, 2013, 11 pages.

Bala et al., "Interaction of Different Metal Ions with Carboxylic Acid Group: A Quantitative Study," The Journal of Physical Chemistry A, 111:28 (6183-6190), Jun. 2007, 8 pages.

bayspec.com [online], "SuperGamut NIR Spectrometer," available on or before Feb. 2014, [retrieved Apr. 18, 20180], retrieved from: URL <http://www.bayspec.com/wp-content/uploads/2014/02/BaySpec-Datasheet-nir-swir.pdf>, 6 pages.

Beck et al., "The Effect of Rheology on Rate of Penetration," SPE/IADC 29368, Society of Petroleum Engineers, Drilling Conference., Jan. 1995, 9 pages.

Bég et al., "Experimental study of improved rheology and lubricity of drilling fluids enhanced with nano-particles", Applied Nanoscience., Jun. 2018, 8(5): 1069-1090, 22 pages.

Bell et al., "Subsurface Discrimination Using Electromagnetic Induction Sensors," IEEE Transactions on Geoscience and Remote Sensing, 39:6, Jun. 2001, 8 pages.

Biswas et al., "Semidefinite Programming Approaches for Sensor Network Localization with Noisy Distance Measurements," IEEE Trans. on Automation Science and Engineering, 3:4 (360-371), Oct. 2006, 12 pages.

Blunt, "Effects of heterogeneity and wetting on relative permeability using pore level modeling", SPE Journal 2:01 (70-87), Mar. 1997.

Boman, "DAS technology expands fiber optic applications for oil, gas industry," Rigzone, May 4, 2015, 4 pages.

Bryant and Blunt, "Prediction of relative permeability in simple porous media" Phys. Rev. A 46:4 (2004-2011), Aug. 1992.

Chappell and Lancaster, "Comparison of methodological uncertainties within permeability measurements" Hydrological Processes 21:18 (2504-2514), Jan. 2007.

Chen et al., "Aggregation Kinetics of Alginate-Coated Hematite Nanoparticles in Monovalent and Divalent Electrolytes," Environmental Science & Technology, 40:5 (1516-1523), Mar. 2006.

Chen et al., "Distributed Source Localization in Wireless Underground Sensor Networks," arXIiv: 1112.4035v1, Dec. 17, 2011, 21 pages.

Chen et al., "Hydration Repulsion between Carbohydrate Surfaces Mediated by Temperature and Specific Ions," Scientific Reports, 6: 1-10, Jun. 23, 2016, 10 pages.

Cole et al., "Polyethylene Glycol Modified, Cross-Linked Starch-Coated Iron Oxide Nanoparticles for Enhanced Magnetic tumor Targeting," Biomaterials, 32:8 (2183-2193), Mar. 1, 2011, 11 pages.

Colombo and McNeice, "Quantifying surface-to-reservoir electromagnetics for waterflood monitoring in a Saudi Arabian carbonate reservoir," Geophysics 78:6, Nov. 2013, 17 pages.

commons.wikimedia.org, [online], "File:6DOF.svg," retrieved from URL <https://commons.wikimedia.org/w/index.php?curid=38429678>, retrieved on Aug. 25, 2020, available on or before Feb. 16, 2015, 5 pages.

Costa et al., "Distributed Weighted-Multidimensional Scaling for Node Localization in Sensor Networks," ACM Trans. Sen. Netw., 2:1 (39-64), Feb. 2006, 26 pages.

Cui et al., "Cross-Layer Energy and Delay Optimization in Small-Scale Sensor Networks," IEEE Transactions on Wireless Communications, 6:10, Oct. 2007, 12 pages.

Danfoss, "Facts Worth Knowing about Frequency Converters," Handbook VLT Frequency Converters, Danfoss Engineering Tomorrow, 180 pages.

De et al., "An Integrated Cross-Layer Study of Wireless CDMA Sensor Networks," IEEE Journal on Selected Areas in Communications, 22:7, Sep. 2004, 15 pages.

DiCarlo et al., "Three-phase relative permeability of water-wet, oil-wet, and mixed-wet sandpacks" SPE Journal 5:01 (82-91), Mar. 2000.

Dixit et al., "A pore-level investigation of relative permeability hysteresis in water-wet systems" SPE Journal 3:02 (115-123), Jun. 1998.

Fatt, "The network model of porous media" Petroleum Transactions 207: 144-181, Dec. 1956.

Gonzalez et al., "Development of an in-tank tuning fork resonator for automated viscosity/density measurements of drilling fluids," IEEE Access, Jan. 2021, 9:25703-25715.

Gonzalez et al., "Viscosity and density measurements using mechanical oscillators in oil and gas applications," IEEE Transactions on Instrumentation and Measurement, Apr. 2018, 67(4):804-810.

Gowida et al., "Data-Driven Framework to Predict the Rheological Properties of CaC12 Brine-Based Drill-in Fluid Using Artificial Neural Network," Energies, 2019, 12, 1880, 33 pages.

Gulbahar et al., "A Communication Theoretical Modeling and Analysis of Underwater Magneto-Inductive Wireless Channels," IEEE Transactions on Wireless Communications, 11:9, Sep. 2012, 9 pages.

Heiba et al., "Percolation theory of two-phase relative permeability" SPE Reservoir Eng. 7:01 (123-132), Feb. 1992.

Hui and Blunt, "Effects of wettability on three-phase flow in porous media" J. Phys. Chem. 104:16 (3833-3845), Feb. 2000.

hunting-itl.com, [online], "Mechanical Centralizers and Decentralizers," retrieved from URL <http://www.hunting-intl.com/titan/wireline-hardware-and-accessories/mechanical-centralizers-and-

(56) References Cited

OTHER PUBLICATIONS decentralizers>, retrieved on Aug. 25, 2020, available on or before Mar. 2015 via Wayback Machine URL <https://web.archive.org/web/20150322210006/http://www.hunting-intl.com/titan/wireline-hardware-and-accessories/mechanical-centralizers-and-decentralizers>, 1 page.
Jacobs et al., "Downhole fiber-optic monitoring: an evolving technology," Society of Petroleum Engineers, Journal of Petroleum Technology 66:08, Aug. 2014, 2 pages, Abstract only.
Ji et al., "Beyond Convex Relaxation: A Polynomial-Time Non-Convex Optimization Approach to Network Localization," Proceedings IEEE INFOCOM, 2499-2507, Apr. 2013, 9 pages.
Kannan et al., "Analysis of Flip Ambiguities for Robust Sensor Network Localization," IEEE Trans. Veh. Technol., 59:4 (2057-2070), May 2010, 14 pages.
Karalis, "Efficient Wireless Non-Radiative Mid-Range Energy Transfer," Annals of Physics 323: 34-48, 2008.
Kisseleff et al., "Throughput of the Magnetic Induction Based Wireless Underground Sensor Networks: Key Optimization Techniques," IEEE Transactions on Communications, 62:12, Dec. 2014, 14 pages.
Kramer, "Water-Soluble Dendritic Architectures with Carbohydrate Shells for the Templation and Stabilization of Catalytically Active Metal Nanoparticles," published by ACS, Macromolecules, 38:20 (8308-8315), Aug. 27, 2005, 8 pages.
Larson III et al., "Modified Butterworth-Van Dyke circuit for FBAR resonators and automated measurement system," 2000 IEEE Ultrasonics Symposium Proceedings. An International Symposium (Cat. No. 00CH37121), Oct. 2000.
Li et al., "In Situ Estimation of Relative Permeability from Resistivity Measurements," Petroleum Geoscience, 20: 143-151, 2014, 10 pages.
Li, "Collaborative Localization with Received-Signal Strength in Wireless Sensor Networks," IEEE Trans. Veh. Technol., 56:6 (3807-3817), Nov. 2007, 11 pages.
Lin et al., "A Tutorial on Cross-Layer Optimization in Wireless Networks," IEEE Journal on Selected Areas in Communications, 24:8, Aug. 2006, 12 pages.
Lin et al., "Magnetic Induction-Based Localization in Randomly-Deployed Wireless Underground Sensor Networks," IEEE Internet of Things Journal, 1-11, Jul. 20, 2017, 11 pages.
machinedesign.com [online], Frances Richards, "Motors for efficiency: Permanent-magnet, reluctance, and induction motors compared," Apr. 2013, retrieved on Nov. 11, 2020, retrieved from URL <https://www.machinedesign.com/motors-drives/article/21832406/motors-for-efficiency-permanentmagnet-reluctance-and-induction-motors-compared>.
Mahmud et al. "Effect of network topology on two-phase imbibition relative permeability" Transport in Porous Media 66:3 (481-493), Feb. 2007, 14 pages.
Martinez et al., "Polysaccharide-based Nanoparticles for Controlled Release Formulations," The Delivery of Nanoparticles, 185-222, May 2012, 39 pages.
Masihpour et al., "Multihop Relay Techniques for Communication Range Extension in Near-Field Magnetic Induction Communication Systems," Journal of Networks, 8:5, May 2013, 13 pages.
Nagy et al., "Comparison of permeability testing methods" Proceedings of the 18th International Conference on Soil Mechanics and Geotechnical Engineering, pp. 399-402, 2013, 4 pages.
Nie, "Sum of Squares Method for Sensor Network Localization," Computational Optimization and Applications, 43:2 (151-179), 2007, 29 pages.
Niewiadomska-Szynkiewicz, "Localization in Wireless Sensor Networks: Classification and Evaluation of Techniques," Int. J. Appl. Mat. Comput. Sci., 22:2 (281-297), 2012, 17 pages.
olympus-ims.com [online], "Thickness and flaw inspection solutions: Electromagnetic acoustic transducer (EMAT)," retrieved on Feb. 8, 2022, retrieved from URL <https://www.olympus-ims.com/en/ultrasonic-transducers/emat/>, 3 pages.
omega.com [online], "Clamp-On Transit Time Ultrasonic Flow Meter," 2019, retrieved on Feb. 8, 2022, retrieved from URL <https://www.omega.com/en-us/flow-instruments/flow-meters/ultrasonic-flow-meters/p/FDT-40-Series>, 3 pages.
Optasense.com [online], "Oilfield Services," available on or before Jun. 2, 2015, via Wayback Machine URL <https://web.archive.org/web/20150602040413/http://www.optasense.com/our-solutions/oilfield-services/>, [retrieved Apr. 6, 2018], retrieved from URL <http://www.optasense.com/our-solutions/oilfield-services/>, 1 page.
piceramic.com [online], "Rectangular Bending Elements," available on or before Mar. 31, 2017, via Internet Archive: Wayback Machine URL <https://web.archive.org/web/20170331054949/https://www.piceramic.com/en/products/piezoceramic-components/bending-elements/>, [retrieved Apr. 6, 2018], retrieved from: URL <https://www.piceramic.com/en/products/piezoceramic-components/bending-elements/>, 2 pages.
pi-usa.us [online], "Piezoelectric actuators, piezo transducers: Pieze stacks, flexures, tubes, benders, shear actuators . . . ," 2022, retrieved on Feb. 8, 2022, retrieved from URL <https://www.pi-usa.us/en/products/piezo-actuators-stacks-benders-tubes/>, 19 pages.
Pompili et al., "A Multimedia Cross-Layer Protocol for Underwater Acoustic Sensor Networks," IEEE Transactions on Wireless Communications, 9:9, Sep. 2010, 10 pages.
Purcell "Capillary pressures—their measurement using mercury and the calculation of permeability therefrom" Journal of Petroleum Technology 1:02 (39-48), Feb. 1949.
Rahmani et al., "Characterizing Reservoir Heterogeneities Using Magnetic Nanoparticles," SPE Reservoir Simulation Symposium, May 2015, 29 pages.
Rio-lasers.com [online], "Redfern Integrated Optics (RIO) Colorado Tunable Laser Source," available on or before Sep. 1, 2016, via Wayback Machine URL <https://web.archive.org/web/20160901172454/http://www.rio-lasers.com/pdf/Rio_Colorado_Product%20Brief_1.24.14.pdf> [retrieved Apr. 6, 2018], retrieved from URL <http://www.rio-lasers.com/pdf/Rio_Colorado_Product Brief_1.24.14.pdf>, 2 pages.
Saeki et al., "Upper and lower critical solution temperatures in poly(ethylene glycol) solutions," Polymer, 17:8 (685-689), Aug. 1976, 5 pages.
Sbl.com [online], "Distributed Acoustic Sensing Technology," available on or before Feb. 11, 2017, via Wayback Machine URL <https://web.archive.org/web/20170211002616/https://www.slb.com/services/characterization/geophysics/wireline/distributed-acoustic-seismic-sensing.aspx>, [retrieved on Apr. 6, 2018], retrieved from URL <https://www.slb.com/services/characterization/geophysics/wireline/distributed-acoustic-seismic-sensing.aspx>, 1 page.
Sedlar et al., "Optical fiber magnetic field sensors with ceramic magnetostrictive jackets," Applied Optics, 35:27, Sep. 20, 1996, 2 pages, abstract only.
Shamsijazeyi et al., "Polymer-Coated Nanoparticles for Enhance Oil Recovery," Journal of Applied Polymer Science, 131:15, Aug. 5, 2014, 13 pages.
Simonetto et al., "Distributed Maximum Likelihood Sensor Network Localization," IEEE Transactions on Signal Processing, 62:6 (1424-1437), Mar. 15, 2014, 14 pages.
Simpson et al., "A Touch, Truly Multiphase Downhole Pump for Unconventional Wells," SPE-185152-MS, Society of Petroleum Engineers (SPE), presented at the SPE Electric Submersible Pump Symposium, the Woodlands, Texas, Apr. 24-28, 2017, 20 pages.
Steminc.com [online], "Piezo Ceraminc Plate 26×8×0.7mm 108 KHz," available on or before Dec. 30, 2013, via Internet Archive Wayback Machine URL <https://web.archive.org/web/20131230010212/https://www.steminc.com/PZT/en/piezo-ceraminc-plate-26x8x7mm-108-khz>, [retrieved on Apr. 6, 2018], retrieved from URL <https://www.steminc.com/PZT/en/piezo-ceraminc-plate-26x8x7mm-108-khz>, 1 page.
Sun et al., "Design of the fiber optic distributed acoustic sensor based on Michelson interferometer and its location application," Optical Engineering, 42, Oct. 1, 2003, 1 pages, Abstract only.
Sun et al., "Optimal Deployment for Magnetic Induction-Based Wireless Networks in Challenged Environments," IEEE Transactions on Wireless Communications, 12:3, Mar. 2013, 10 pages.

(56) References Cited

OTHER PUBLICATIONS

Udd, "An overview of fiber-optic sensors," Review of Science Instruments 66: 4015, Jun. 1995, 16 pages, Abstract only.

Vuran et al., "Communication Through Soil in Wireless Underground Sensor Networks—Theory and Practice," 309-347, 2010, 39 pages.

Vuran et al., "XLP: A Cross-Layer Protocol for Efficient Communication in Wireless Sensor Networks," IEEE Transactions on Mobile Computing, 9:11, Nov. 2010, 14 pages.

Wikipedia.com [online], "Distributed acoustic sensing", Jan. 17, 2012, [retrieved on Feb. 23, 2018], retrieved from URL <https://en.wikipedia.org/wiki/Distributed_acoustic_sensing>, 5 pages.

Wikipedia.org [online], "Ultrasonic flow meter," Sep. 2019, retrieved on Feb. 8, 2022, retrieved from URL <https://en.wikipedia.org/wiki/Ultrasonic_flow_meter>, 3 pages.

Yamamoto, "Imaging the permeability structure within the near-surface sediments by acoustic crosswell tomography," Journal of Applied Geophysics, 47:1, May 2001, 11 pages.

Zhan et al., "Characterization of Reservoir Heterogeneity Through Fluid Movement Monitoring with Deep Electromagnetic and Pressure Measurements," SPE 116328, Society of Petroleum Engineers (SPE), SPE International, presented at the 2008 SPE Annual Technical Conference and Exhibition, Sep. 21-24, 2008, 16 pages.

Zhao et al., "Chromatographic Separation of Highly Soluble Diamond Nanoparticles Prepared by Polyglycerol Grafting," Angewandte Chemie International Edition, 50:6 (1388-1392), Feb. 7, 2011, 5 pages.

\* cited by examiner

FLUID FLOW SENSOR USING DRIVER AND REFERENCE ELECTROMECHANICAL RESONATORS

TECHNICAL FIELD

The present disclosure applies to detecting the viscosity and density of a drilling fluid.

BACKGROUND

While drilling a well, a drilling fluid (or "drilling mud") is pumped downhole through the drill string. The drilling fluid jets out from the drill bit and flows back to the surface, carrying newly-cut rock fragments (or "cuttings") with the fluid. Drilling mud "weight" or density is carefully tuned to keep the pressure at the bottom of the well high enough to prevent fluids in the reservoir from entering the wellbore, but not so high as to damage rock formations. Wellbore balancing is even more critical in complicated reservoirs such as deep-water, horizontal, or branched multilateral wells, where drilling margins (the difference between too much and too little pressure) may be small. Because proper monitoring and control of mud weight is important, benefits for both safety and drilling performance can be realized from automating processes used for monitoring and control of drilling mud weight.

Viscosity of drilling mud is another important parameter which can be optimized in order to maintain safe and efficient operation. Viscosity affects drilling hydraulics and is tuned to optimize the rate of penetration, balancing how fast cuttings can be lifted versus the potentially damaging shear forces on the wellbore wall.

The flow rate of drilling mud is another critical parameter for drilling operations, as the flow rate is used to determine total amounts of drilling mud that enter and exit a wellbore. Accounting for the balance of drilling mud entering and exiting the wellbore can indicate problems downhole, whether the problems are caused by changes in flow impedance, washouts downhole creating total fluid losses, or fluid incursion from the downhole formation into the drilling mud returning from the well. Monitoring the flow rate of drilling mud is important for the detection and prevention of blow-outs. Flow rate is also a confounding parameter for density and viscosity measurements performed in situ, as these fluid parameters may depend on the flow rate of the drilling mud. Flow rates of drilling mud are conventionally measured by: drilling mud pump speed, mechanical flow sensing devices (such as paddle-meters/turbines/floats), extrapolation of flow rates based on pressure drop between elements in the mud circulation system, pit level meters, acoustic level meters, magnetic flowmeters, and J-pipe strain sensors.

Drilling mud pump speed measurements can provide information on the flow rate of the drilling mud at the inflow of the drilling circulation system. However, drilling mud flow rate is a function of: pump speed, physical properties of the mud, efficiency of the pump, line pressure of the mud system, seal wear, and temperature. The absolute accuracy of this measurement method is usually insufficient to detect fluid flow problems before they become catastrophic to the integrity of a drilling operation. Additionally, drilling mud pump speed provides flow rate measurements at one location only. If there is a localized problem in the drilling circulation, such as fluid loss or intrusion, then the drilling mud pump speed measurement may not indicate the source of the fluid loss or intrusion.

Mechanical flow sensing devices can provide information on the flow rate of drilling mud at the inflow and outflow of the drilling circulation system. Flow sensing devices can include, for example: turbines, paddle-meters, and flotation arms that change angle with flow rate. There is a limited number of these devices that can operate on the inflow of the drilling circulation system due the elevated pressure of the fluid. Additionally, the flow rate measurements provided by these inflow-capable mechanical devices are sensitive to the physical properties of drilling mud, e.g., changes in viscosity can confound their measurement accuracy. These devices are also susceptible to mechanical failure, as they contain moving parts and can become clogged by the particle suspensions within drilling mud. Mechanical flow sensing devices that operate on the outflow of the drilling circulation system are susceptible to changes in the height of the fluid where the measurement is made. Mechanical systems are especially susceptible to mechanical failures at outflow measurements, as the returning mud contains more abrasive elements and rock cuttings that can erode the mechanical components.

Drilling mud flow rates can be measured by extrapolating flow from a given pressure drop across elements in the drilling circulation system. This method can suffer from sensitivity to the physical parameters of the flow, such as: density, viscosity, empirically fit friction factors of the piping that may vary with the Reynolds number of the fluid flow, and the flow regime of drilling mud flowing through the system.

Pit level meters can indicate differences in the inflow vs. outflow of the drilling mud circulation system. Changes in the height of the drilling mud pit can be measured over a fixed amount of time, and a difference in flow rates can be calculated. These are inherently an integrated measurement, and do not provide real-time monitoring of the flow rates for timely corrections to the drilling system parameters to be applied.

Acoustic level meters can provide flow rate measurements. These systems monitor the height of the drilling mud at certain points in the drilling circulation systems and extrapolate flow rate from changes in the fluid height. These systems require accurate monitoring of temperature and composition above the drilling mud in the line, as compensation for these effects is necessary for accurate flow rate estimation.

Magnetic flowmeters are capable of measuring mud flow rates at the inflow and outflow of the drilling circulation system. However, these systems typically require pipe sections which are completely filled with drilling mud. This adds complication to the drilling circulation system, as U-pipe sections must be installed and periodically cleaned of cuttings accumulation in the bottom of the U-pipe. Additionally, these systems are not able to accurately resolve flow rate for non-conductive oil-based drilling muds.

J-pipe strain sensors are also capable of measuring drilling mud flow rates at the inflow and outflow of the drilling circulation system. These systems require the installation of a J-pipe section in the line to be measured. Additionally, they require continuous monitoring of the density of the fluid moving through the meter.

SUMMARY

The present disclosure describes techniques for using a fluid sensor to detect the viscosity and density of a drilling fluid. In some implementations, a computer-implemented method includes the following. A driver and a reference are monitored for responses by a measurement controller of a system for measuring fluid flow. The driver is configured as a driving electromechanical resonator for contacting a drilling fluid in a well. The reference is configured as a reference electromechanical resonator for contacting the drilling fluid in the well. The reference is of a similar construction as the driver and is in contact with the drilling fluid in a substantially same way. Real-time measurements are performed by the measurement controller based on information received from the driver and the reference. A viscosity and a density of the drilling fluid are determined by the measurement controller based on the real-time measurements and the similar construction. The similar construction of the driver and the reference enables the measurement controller to mitigate environmental sensitivities of the driver and the reference and to enhance fluid property sensitivities by the driver and the reference to physical properties of the drilling fluid.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The subject matter described in this specification can be implemented in particular implementations, so as to realize one or more of the following advantages. Environmental parameters of a drilling fluid, such as pressure, temperature, and fluid velocity, are mitigated when density and viscosity measurements of the fluid are determined. For example, a similar construction of the driver and the reference can result in a reduced sensitivity to pressure and temperature changes and can provide an additional capability to measure fluid velocity. The response of the reference to changes in the environmental properties of the fluid can be used to cancel out a parasitic element in the driver that also changes in response to environmental properties of the fluid such that the system is better able to measure density and viscosity in viscous fluids. The use of a reference and driver both in contact with the fluid enables the system to measure the flow velocity of the drilling fluid at the measurement site using acoustic-based methods.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

Figure 1:
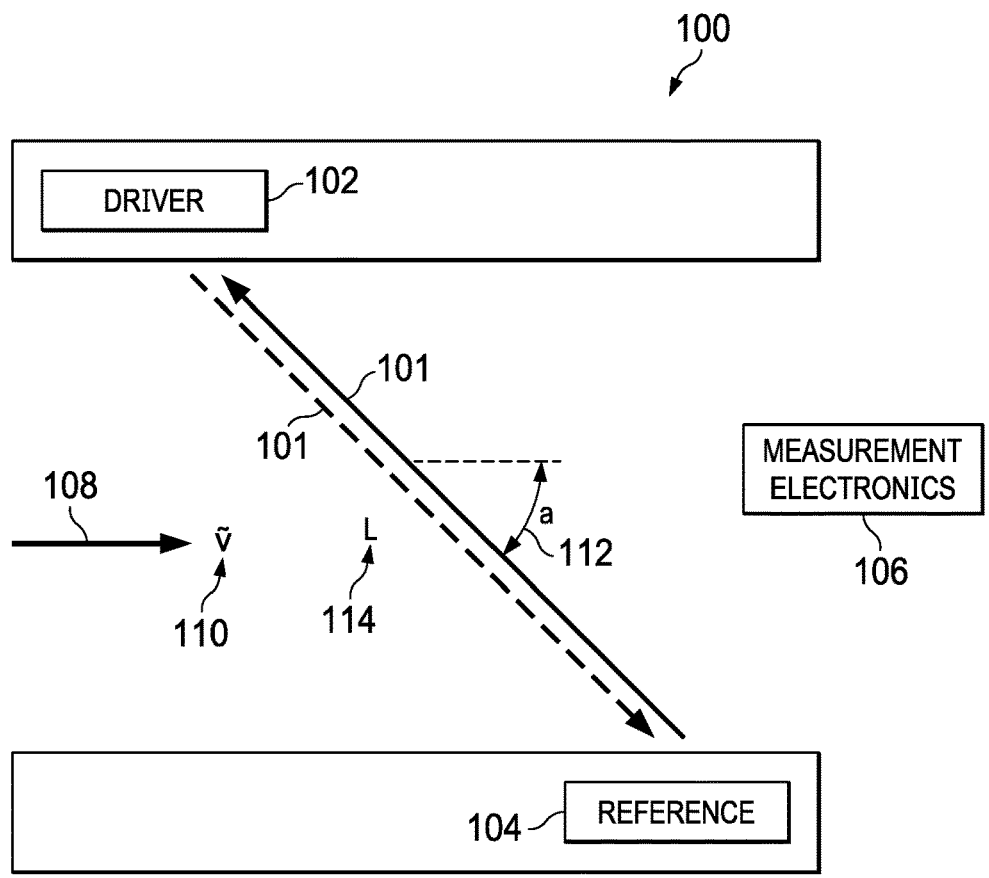
FIG. 1 is a diagram showing an example of an electromechanical resonator system used to measure physical properties of fluids, according to some implementations of the present disclosure.

The following detailed description describes techniques for using a fluid sensor to detect the viscosity and density of a drilling fluid. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

The present disclosure relates a fluid sensor used to detect the viscosity and density of a drilling fluid. The density and viscosity measurements of similar fluid sensors are affected by environmental parameters of the drilling fluid, such as: pressure, temperature, and fluid velocity. The fluid sensor described in this disclosure has reduced sensitivity to pressure and temperature changes and has additional capability to measure fluid velocity. The fluid sensor includes a driving electromechanical resonator (or a "driver"), a reference electromechanical resonator (or a "reference"), and measurement electronics. The driver and reference are of similar construction and in contact with the drilling fluid in substantially the same way. The measurement electronics are electrically coupled to the driver and the reference to perform in situ measurements based on information received from the driver and the reference. Specifically, the measurement electronics monitor the response of the driver and reference to mitigate environmental sensitivity and enhance the sensitivity to physical properties of the fluid. The response of the reference to changes in the environmental properties of the fluid is used to cancel out a parasitic element in the driver that also changes in response to environmental properties of the fluid such that the system is better able to measure density and viscosity in viscous fluids. The use of a reference and driver both in contact with the fluid enables the system to measure the flow velocity of the drilling fluid at the measurement site using acoustic-based methods. In some implementations, the driver faces the reference so that acoustic pulses travel directly between the driver and the reference. In other implementations, both the driver and the reference reside on a common plane with both facing a reflector, so that acoustic pulses travel between the driver and the reference by bouncing off the reflector. The fluid velocity information from the sensor is an additional measurement of the system to log/report, and can also be used to normalize the viscosity measurements of the system in nonlinear (velocity-dependent viscosity) drilling fluids.

In some implementations, a device can be used that is capable of measuring flow rate of the drilling mud, in addition to simultaneously measuring density and viscosity of the drilling mud, which does not have the limitations of conventional solutions. These limitations include: susceptibility to physical parameters of the fluid, installation of additional hydraulic and/or measurement elements into the drilling circulation system, integrated measurements that do not provide instantaneous measurements of flow, and inability to measure both the inflow and outflow of the drilling circulation system.

In some implementations, the driver faces the reference so that acoustic pulses travel directly between the driver and the reference. In some implementations, the system includes a reflector that is configured to reflect acoustic pulses. In this case, the driver and the reference face the reflector so that acoustic pulses travel between the driver and the reference by bouncing from the reflector. In some implementations, the driver and the reference reside on a common plane. In some implementations, the operations further include: capturing, by the measurement controller, fluid velocity information for the drilling fluid; and normalizing viscosity measurements, by the measurement controller, nonlinear, velocity-dependent viscosity drilling fluids.

In some implementations, a computer-implemented system can be used for measuring fluid flow. The system (for example, the system of FIG. 1) can include a driver configured as a driving electromechanical resonator for contacting a drilling fluid in a well. The system can also include a reference configured as a reference electromechanical resonator for contacting the drilling fluid in the well. The reference can be of a similar construction as the driver and can be in contact with the drilling fluid in a substantially same way. A measurement controller electrically coupled to the driver and the reference can be configured to provide measurement electronics for sensing fluid flow. The system can include one or more processors and a non-transitory computer-readable storage medium coupled to the one or more processors and can store programming instructions for execution by the one or more processors to perform operations including the following. Responses from the driver and the reference are monitored by the measurement controller. Based on the similar construction of the driver and the reference, the measurement controller can mitigate environmental sensitivities of the driver and the reference and can enhance fluid property sensitivities by the driver and the reference to physical properties of the drilling fluid. Real-time measurements are performed by the measurement controller based on information received from the driver and the reference. A viscosity and a density of the drilling fluid are determined by the measurement controller based on the real-time measurements.

FIG. 1 is a diagram showing an example of an electromechanical resonator system 100 used to measure physical properties of fluids, according to some implementations of the present disclosure. The measured physical properties can include viscosity and density, for example. The system 100 can utilize a driving electromechanical resonator (e.g., driver 102) to interrogate the fluid. Parasitic environmental response from the driver 102 adversely affects the sensitivity of the system to physical properties of the fluid. A reference electromechanical resonator (e.g., reference 104) with the same sensing element design as the driver 102 is integrated into the system. The reference 104 experiences the same environment as the driver 102, e.g., temperature and pressure change, but is insensitive to physical properties of the fluid. By monitoring the response of the driver 102 and the reference 104, the environmental sensitivity is mitigated, and the sensitivity to physical properties of the fluid are enhanced.

The driver 102 is an electromechanical resonator in contact with the fluid and which oscillates within the fluid. Density and viscosity of the fluid are measured by monitoring the oscillation frequency and oscillation bandwidth of the driver 102 through the use of measurement electronics 106. Examples of driver 102 electromechanical resonators include piezoelectric actuators and electromagnetic acoustic transducers.

The reference 104 is an electromechanical resonator of similar construction to the driver 102 that is in contact with the fluid. The reference 104 is used to mitigate environmental effects on the response of the driver 102, e.g., changes in temperature and/or pressure of the fluid. Examples of electromechanical resonators include piezoelectric actuators and electromagnetic acoustic transducers).

In some implementations, electromechanical resonator behavior can be modeled using a Butterworth Van Dyke equivalent circuit. In this model, the bulk capacitance of the material behaves as a parallel capacitance that reduces the overall energy coupled into the resonator. If the reference 104 is of the same construction as the driver 102 element and is coupled to the fluid in a similar way such that it experiences the same temperature and pressure, then the reference 104 can be used to cancel out the effect of the parallel capacitance that reduces the energy coupled into the resonator.

Flow rate measurements can occur by issuing acoustic pulses from the driver 102 to the reference 104, and vice versa. The density and viscosity measurement process can occur simultaneously or separately from fluid flow rate measurements.

In some implementations, the driver 102 and the reference 104 of the electromechanical resonator system can measure flow using a delay time in acoustic pulse propagation (similar to an ultrasonic flow meter). The driver 102 and the reference 104 can be implemented as piezo actuators coupled to a diaphragm that is contact with the fluid to be interrogated. The driver 102 and the reference 104 can be displaced on opposite sides of a fixed geometry, such as a pipe. An acoustic pulse is transmitted into the fluid by the driver 102 element. The pulse travels through the fluid and is received at the reference 104 with a time delay between transmission and reception of time $t_D$. Similarly, an acoustic pulse is transmitted into the fluid by the reference 104. This pulse travels through the fluid, and is received at the driver 102 element with a time delay between transmission and reception of time $t_R$.

As shown in FIG. 1, acoustic pulses 101 are issued from the driver 102 to the reference 104, and vice-versa. The travel time of pulses is sped up or slowed down by the projection of the fluid velocity 110 along the angle of the pulse propagation a 112, at a distance L 114 between measurement elements. Fluid flow direction is indicated by arrow 108. In the arrangement of the electromechanical resonator system of FIG. 1, the fluid is flowing from the left to the right. In this case, the velocity of the fluid decreases the time delay of the acoustic pulse $t_D$, such that:

$$t_D = \frac{L}{c + \tilde{v} \cdot \cos\alpha} \quad (1)$$

Similarly, the velocity of the fluid will increase the time delay of the acoustic pulse $t_R$, such that:

$$t_R = \frac{L}{c - \tilde{v} \cdot \cos\alpha} \quad (2)$$

where L is the travel distance between the driver 102 and the reference 104, c is the sound speed of the acoustic pulse through the fluid, $\tilde{v}$ is the velocity of the fluid flow, and $\alpha$ is the angle of the acoustic pulse with respect to the direction of flow. The sound speed is typically unknown for the measured fluid and is a strong function of fluid temperature $T_i$, density $\rho_i$, and compressibility.

If the acoustic pulse travel time measurements transmitted by the driver 102 and the reference 104 are issued within a short time of each other, e.g., within ≤1 second, then it is assumed that the sound speed of the fluid and the fluid velocity of the fluid are the same in both measurements. Thus, the fluid velocity is calculated as:

$$\tilde{v} = \frac{L(t_R - t_D)}{2 t_R t_D \cos\alpha} \quad (3)$$

which is independent of the fluid sound speed c. This geometry of flow measurement can be implemented in an open volume of fluid, e.g., inserted into a tank of fluid or a closed volume of fluid, e.g., integrated into a section of pipe.

In some implementations, the driver 102 and the reference 104 of the electromechanical resonator system measure flow using a delay time in acoustic pulse propagation, similar to the embodiment described above. In this instance, the driver 102 and the reference 104 are displaced on the same side of a fixed geometry, such as a liquid-tight housing. An acoustic pulse is transmitted into the fluid by the driver 102 element. This pulse travels through the fluid, where it encounters a reflecting surface. The acoustic pulse reflects off of this surface, continues traveling through the fluid, and is then received at the reference 104 with a time delay between transmission and reception of time $t'_D$. Similarly, an acoustic pulse is transmitted into the fluid by the reference 104. This pulse travels through the fluid, reflects off of the same surface, and is received at the driver 102 element with a time delay between transmission and reception of time $t'_R$.

Figure 2:
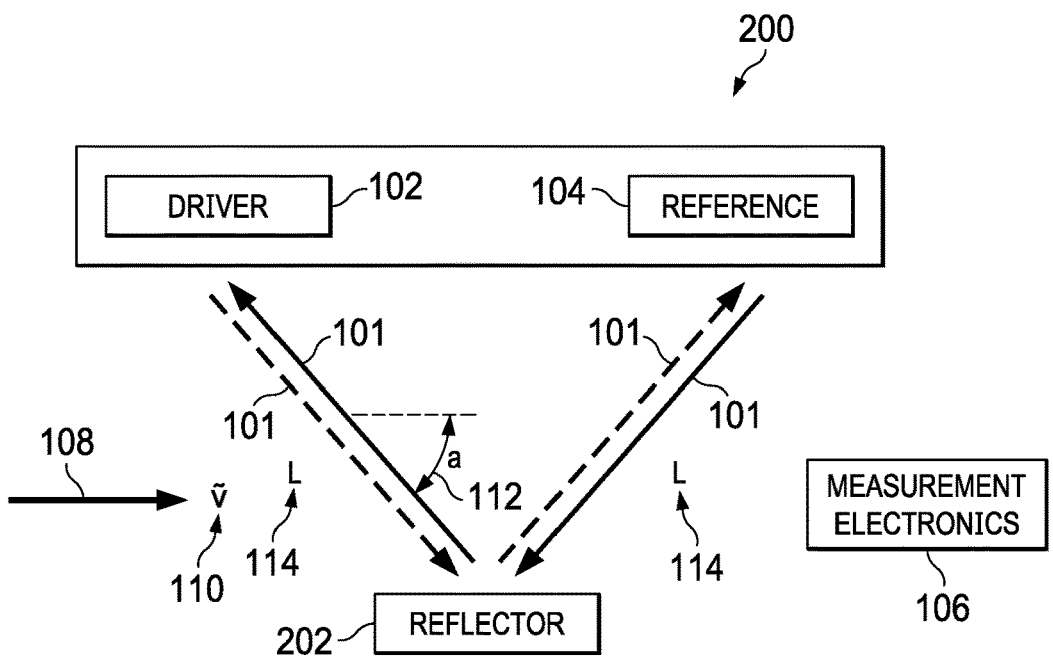
FIG. 2 is a diagram of an example of acoustic pulses issued from a driver to a reference and vice-versa, encountering a reflecting element in their path, according to some implementations of the present disclosure.

FIG. 2 is a diagram of an example of acoustic pulses issued from a driver 102 to a reference 104 and vice-versa, encountering a reflecting element (reflector 202) in their path, according to some implementations of the present disclosure. The travel time of pulses is sped up or slowed down by the projection of the fluid velocity $\tilde{v}$ along the angle of the pulse propagation $\alpha$, at a distance 2L between measurement elements. Fluid flow direction is indicated by arrow 108.

In the example arrangement of the electromechanical resonator system shown in FIG. 2, the fluid is flowing from the left to the right. In this case, the velocity of the fluid will decrease the time delay of the acoustic pulse $t'_D$, such that:

$$t'_D = \frac{2L}{c + \tilde{v} \cdot \cos\alpha} \quad (4)$$

Similarly, the velocity of the fluid will increase the time delay of the acoustic pulse $t'_R$ such that:

$$t'_R = \frac{2L}{c - \tilde{v} \cdot \cos\alpha} \quad (5)$$

where 2L is the travel distance between the driver 102 and the reference 104, c is the sound speed of the acoustic pulse through the fluid, $\tilde{v}$ is the velocity of the fluid flow, and $\alpha$ is the angle of the acoustic pulse with respect to the direction of flow. The sound speed is typically unknown for the measured fluid and is a strong function of fluid temperature $T_i$, density $\rho_i$, and compressibility.

If the acoustic pulse travel time measurements transmitted by the driver 102 and the reference 104 are issued within a short time of each other, then it is assumed that the sound speed of the fluid and the fluid velocity of the fluid are the same in both measurements. Thus, the fluid velocity is calculated as:

$$\tilde{v} = \frac{L(t'_R - t'_D)}{t'_R t'_D \cos\alpha} \quad (6)$$

which is independent of the fluid sound speed c. This geometry of flow measurement can be implemented in an open volume of fluid, e.g., inserted into a tank of fluid, or a closed volume of fluid, e.g., integrated into a section of pipe. The reflecting element can be a bluff body integrated into an immersible housing containing the driver 102 and the reference 104. In another example, the reflecting element can be a wall surface of a tank of fluid. In another example, the reflecting element can be separated phases of fluid with different acoustic impedances such that the interface between the fluids acts as a reflector. In another example, the reflector can be the wall surface of a closed volume pipe.

In the present disclosure, the reference electromechanical resonator is described as an assembly of "similar construction" as the driver electromechanical resonator. Also, the reference electromechanical resonator is placed in direct contact with the fluid being interrogated by the driver. The implication with this "similar construction" term is that the assembly containing the mechanical elements in contact with the fluid, the piezoelectric resonator (coupled to the mechanical elements in contact with the fluid and pre-load force imparted on the piezo in order to constrain the motion of the piezo resonator & couple the resonator to the mechanical elements in contact with the fluid) shall be the same as the driver electromechanical resonator. In this way, the piezoelectric resonator of the reference experiences the same temperature and strain as the piezoelectric resonator in the driver at the same moment in time. As a result, the reference electromechanical resonator has exactly the same parasitic capacitance value for complete cancellation in the measurement circuit. A further modification can be made to the reference mechanical elements in contact with the fluid. For example, the mechanical cantilever/tuning-fork resonance can be removed or altered in order to remove effects of the dynamic strain sensitive to the fluid properties from imparting spurious changes in the piezoelectric resonator voltages/currents in the bandwidth of the driver measurement.

As this system now contains two electromechanical resonators in contact with the fluid, acoustic-based fluid velocity measurements can be realized with the two resonators. The velocity of the drilling fluid at the sensor is an important characteristic to monitor. Operators can use this fluid velocity measurement as a source of feedback and/or totalization in the drilling fluid system. The fluid velocity is also a parameter of interest in understanding the dynamic viscosity of the shear-thinning drilling fluids as the viscosity measured by this system is also a function of the velocity of the fluid at the measurement location.

Two implementations of acoustic-based fluid velocity measurements with the driver and reference system are possible: 1) acoustic pulses travel from the driver 102 to the reference 104 in a direct path, or 2) acoustic pulses travel from the driver 102 to the reference 104 in a reflected path.

The driver 102 and the reference 104 are equally sensitive to the environment. As a result, the parasitic elements that reduce the sensitivity and dynamic range of the driver in viscous fluids can be completely canceled out by a differencing process between the electrical response of the driver 102 and the reference 104.

Figure 3:
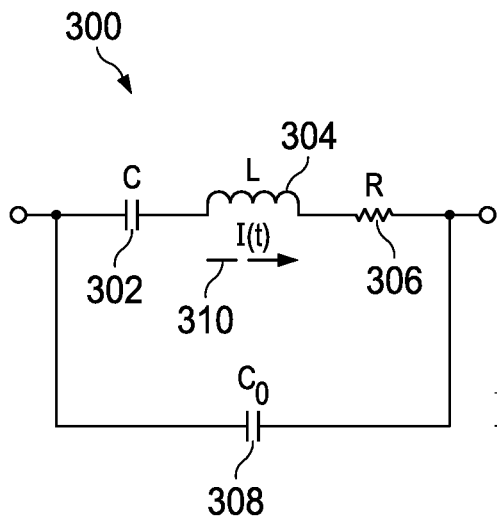
FIG. 3 is a diagram showing an example of a Butterworth Van Dyke (BVD) equivalent model 300 of an electromechanical resonator, according to some implementations of the present disclosure.

FIG. 3 is a diagram 300 showing an example of a Butterworth Van Dyke (BVD) equivalent model 300 of electromechanical resonator, according to some implementations of the present disclosure. The diagram 300 shows the model that is used in conventional systems, showing an equivalent electrical model of a mechanical resonator coupled to a piezoelectric material. The mechanical resonator capacitance C 302, mechanical resonator inductance L 304, and mechanical resonator resistance R 306 represent the electrical equivalent of the motion of the mechanical resonator immersed in the fluid. The parallel capacitance $C_0$ 308 is the bulk capacitance of the piezoelectric dielectric material that is coupled to the mechanical resonator. The piezoelectric material transforms the motion of the mechanical resonator into measurable electric signals. Current traveling through this equivalent network can impart energy into the resonator components (L, C, R) or can be bypassed through the parallel capacitance if the equivalent impedance of the parallel capacitor at frequency is lower than the equivalent impedance of the resonator components. The equivalent impedance, $Z_{EQ}$, of the BVD resonator circuit is:

$$Z_{EQ} = \frac{1}{\frac{1}{Z_{RES}} + \frac{1}{Z_{CO}}} \quad (7)$$

where $Z_{RES}$ is the impedance of the series resonator components (L, C, R), and $Z_{C_0}$ is the impedance of the parallel capacitance. If the impedance of the parallel capacitance is significantly smaller than the impedance of the series resonator components, e.g., $Z_{RES} \ll Z_{C_0}$, then the equivalent impedance will be dominated by the impedance of the parallel capacitance such that $Z_{EQ} \approx Z_{C_0}$. The current through the series resonator components I(t) 310 will be negligible in this case, and very little energy will be imparted into the resonator element. This short path through the parallel capacitance becomes more significant as the viscous losses of the fluid increase, such that the equivalent R increases, and therefore the impedance of the series resonator $Z_{RES}$ increases. Thus, the parallel capacitor acts as a parasitic element that can reduce the amount of energy imparted into the resonator.

This parallel capacitance can be problematic in viscous fluids as the equivalent resonator resistance R becomes large due to the increased viscosity of the fluid. As a result, the equivalent impedance of the resonator components (L, C, R) becomes a less favorable path for current to travel through compared to the bypass path through the parallel capacitance $C_0$. Less energy is imparted into the resonator elements, reducing signal-to-noise ratio of the system to detect properties of the fluid in which the resonator is immersed.

Figure 4:
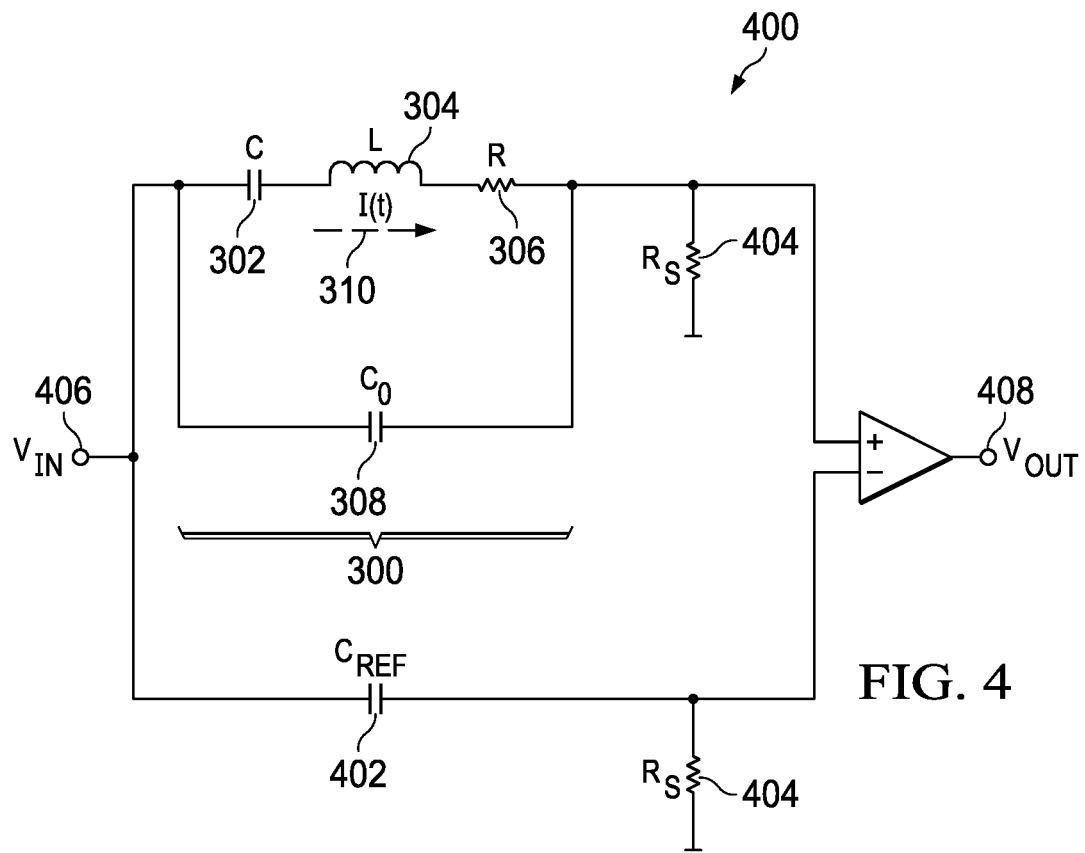
FIG. 4 is a diagram of an example of a circuit to remove the effects of parasitic parallel capacitance in an electromechanical resonator, according to some implementations of the present disclosure.

FIG. 4 is a diagram of an example of a circuit 400 to remove the effects of parasitic parallel capacitance in an electromechanical resonator, according to some implementations of the present disclosure. In this this example, the effect of the parallel capacitance in the transfer function of the system response is removed by subtracting an equivalent capacitance, e.g., the reference 104 capacitance $C_{REF}$ 402. If the parallel capacitance of the reference 104 is exactly the same as the parallel capacitance of the driver 102, then all of the energy imparted into the system excites the resonator. This increases the signal-to-noise ratio and allows the system to detect properties of the fluid in which the resonator is immersed, even in the case of high-viscosity/lossy fluids.

The driver parallel capacitance $C_0$(T, P, F) is a function of the fluid temperature T, fluid pressure P, and preload mass force F. If the reference capacitor $C_{REF}$ is merely a discrete capacitor that is nominally the same value as $C_0$ at some standard condition, then it is not likely to exactly match the capacitance of the parasitic capacitance $C_0$ across the complete environmental range from standard conditions to process conditions. In the present disclosure, an electromechanical resonator of "similar construction" is used that is also in contact with the fluid, so that $C_{REF}$(T, P, F)=$C_0$(T,P, F). The parasitic parallel capacitance elements will exactly match each other for any process condition with the same time constant of change, ensuring the system is able to achieve high signal-to-noise ratios for lossy fluids at any process condition.

In this case, the bulk capacitance of the material is the parallel capacitance of the piezoelectric material coupled to the mechanical resonator. The mechanical resonator capacitance C, mechanical resonator inductance L, and mechanical resonator resistance $R_S$ 404 represent the electrical equivalent of the motion of the mechanical resonator immersed in the fluid. The parallel capacitance $C_0$ is the bulk capacitance of the piezoelectric dielectric material that is coupled to the mechanical resonator. The piezoelectric material transforms the motion of the mechanical resonator into measurable electric signals. The circuit 400 shows voltage in (VIN) 406 and voltage out ($V_{OUT}$) 408.

Figure 5:
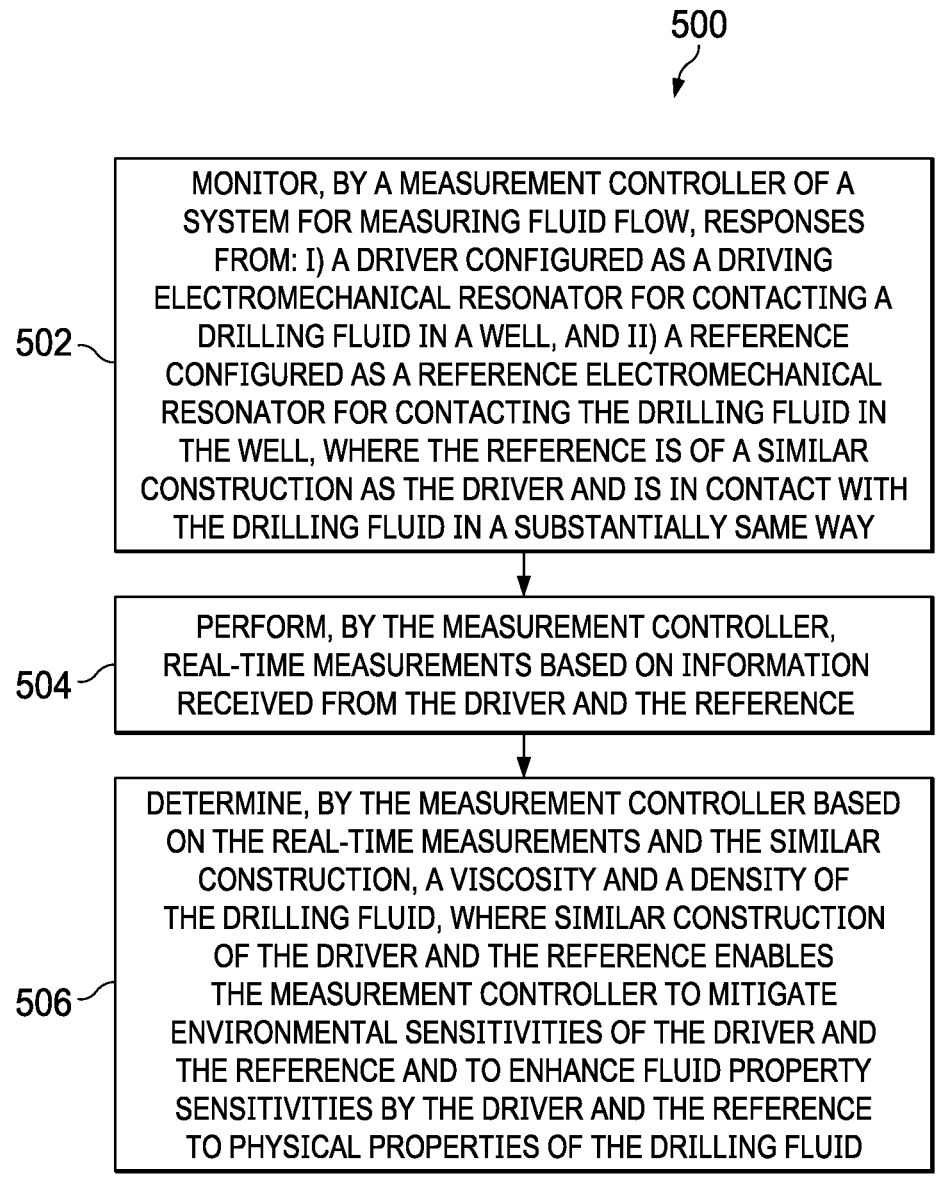
FIG. 5 is a flowchart of an example of a method for determining a density and a viscosity of a drilling fluid using signals sent between a driver and a reference of a similar construction and in contact with the drilling fluid, according to some implementations of the present disclosure.

FIG. 5 is a flowchart of an example of a method 500 for determining a density and a viscosity of a drilling fluid using signals sent between a driver and a reference of a similar construction and in contact with the drilling fluid, according to some implementations of the present disclosure. For clarity of presentation, the description that follows generally describes method 500 in the context of the other figures in this description. However, it will be understood that method 500 can be performed, for example, by any suitable system, environment, software, and hardware, or a combination of systems, environments, software, and hardware, as appropriate. In some implementations, various steps of method 500 can be run in parallel, in combination, in loops, or in any order.

At 502, a driver and a reference are monitored for responses by a measurement controller of a system for measuring fluid flow. The driver is configured as a driving electromechanical resonator for contacting a drilling fluid in a well. The reference is configured as a reference electromechanical resonator for contacting the drilling fluid in the well. The reference is of a similar construction as the driver and is in contact with the drilling fluid in a substantially same way. FIG. 1 shows an example of the driver 102 and the reference 104. From 502, method 500 proceeds to 504.

At 504, real-time measurements are performed by the measurement controller based on information received from the driver and the reference. For example, the measurement controller 106 can perform measurements using real-time information received from the driver 102 and the reference 104. From 504, method 500 proceeds to 506.

At 506, a viscosity and a density of the drilling fluid are determined by the measurement controller based on the real-time measurements and the similar construction. The similar construction of the driver and the reference enables the measurement controller to mitigate environmental sensitivities of the driver and the reference and to enhance fluid property sensitivities by the driver and the reference to physical properties of the drilling fluid. As an example, the measurement controller 106 can determine the viscosity and the density of the drilling fluid. After 506, method 500 can stop.

In some implementations, in addition to (or in combination with) any previously-described features, techniques of the present disclosure can include the following. Customized user interfaces can present intermediate or final results of the above described processes to a user. The presented information can be presented in one or more textual, tabular, or graphical formats, such as through a dashboard. The information can be presented at one or more on-site locations (such as at an oil well or other facility), on the Internet (such as on a webpage), on a mobile application (or "app"), or at a central processing facility. The presented information can include suggestions, such as suggested changes in parameters or processing inputs, that the user can select to implement improvements in a production environment, such as in the exploration, production, and/or testing of petrochemical processes or facilities. For example, the suggestions can include parameters that, when selected by the user, can cause a change or an improvement in drilling parameters (including speed and direction) or overall production of a gas or oil well. The suggestions, when implemented by the user, can improve the speed and accuracy of calculations, streamline processes, improve models, and solve problems related to efficiency, performance, safety, reliability, costs, downtime, and the need for human interaction. In some implementations, the suggestions can be implemented in real-time, such as to provide an immediate or near-immediate change in operations or in a model. The term real-time can correspond, for example, to events that occur within a specified period of time, such as within one minute or within one second. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart, or are located in different countries or other jurisdictions.

Figure 6:
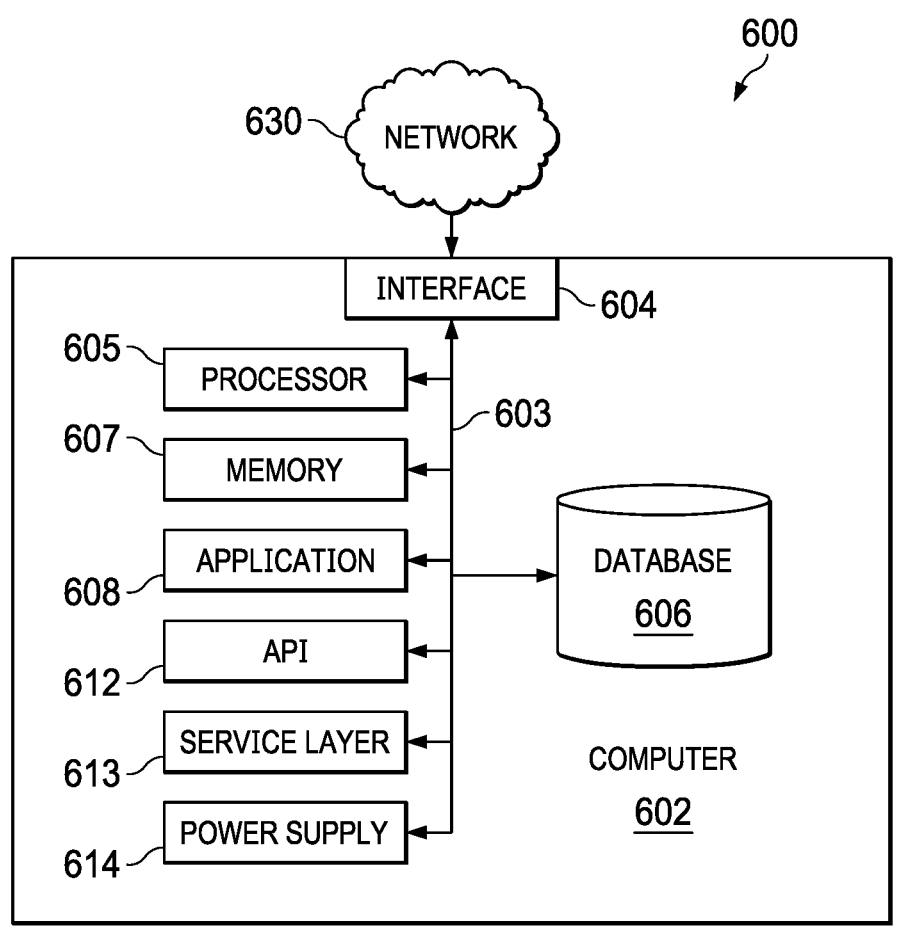
FIG. 6 is a block diagram illustrating an example computer system used to provide computational functionalities associated with described algorithms, methods, functions, processes, flows, and procedures as described in the present disclosure, according to some implementations of the present disclosure.

FIG. 6 is a block diagram of an example computer system 600 used to provide computational functionalities associated with described algorithms, methods, functions, processes, flows, and procedures described in the present disclosure, according to some implementations of the present disclosure. The illustrated computer 602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 602 can include input devices such as keypads, keyboards, and touch screens that can accept user information. Also, the computer 602 can include output devices that can convey information associated with the operation of the computer 602. The information can include digital data, visual data, audio information, or a combination of information. The information can be presented in a graphical user interface (UI) (or GUI).

The computer 602 can serve in a role as a client, a network component, a server, a database, a persistency, or components of a computer system for performing the subject matter described in the present disclosure. The illustrated computer 602 is communicably coupled with a network 630. In some implementations, one or more components of the computer 602 can be configured to operate within different environments, including cloud-computing-based environments, local environments, global environments, and combinations of environments.

At a top level, the computer 602 is an electronic computing device operable to receive, transmit, process, store, and manage data and information associated with the described subject matter. According to some implementations, the computer 602 can also include, or be communicably coupled with, an application server, an email server, a web server, a caching server, a streaming data server, or a combination of servers.

The computer 602 can receive requests over network 630 from a client application (for example, executing on another computer 602). The computer 602 can respond to the received requests by processing the received requests using software applications. Requests can also be sent to the computer 602 from internal users (for example, from a command console), external (or third) parties, automated applications, entities, individuals, systems, and computers.

Each of the components of the computer 602 can communicate using a system bus 603. In some implementations, any or all of the components of the computer 602, including hardware or software components, can interface with each other or the interface 604 (or a combination of both) over the system bus 603. Interfaces can use an application programming interface (API) 612, a service layer 613, or a combination of the API 612 and service layer 613. The API 612 can include specifications for routines, data structures, and object classes. The API 612 can be either computer-language independent or dependent. The API 612 can refer to a complete interface, a single function, or a set of APIs.

The service layer 613 can provide software services to the computer 602 and other components (whether illustrated or not) that are communicably coupled to the computer 602. The functionality of the computer 602 can be accessible for all service consumers using this service layer. Software services, such as those provided by the service layer 613, can provide reusable, defined functionalities through a defined interface. For example, the interface can be software written in JAVA, C++, or a language providing data in extensible markup language (XML) format. While illustrated as an integrated component of the computer 602, in alternative implementations, the API 612 or the service layer 613 can be stand-alone components in relation to other components of the computer 602 and other components communicably coupled to the computer 602. Moreover, any or all parts of the API 612 or the service layer 613 can be implemented as child or sub-modules of another software module, enterprise application, or hardware module without departing from the scope of the present disclosure.

The computer 602 includes an interface 604. Although illustrated as a single interface 604 in FIG. 6, two or more interfaces 604 can be used according to particular needs, desires, or particular implementations of the computer 602 and the described functionality. The interface 604 can be used by the computer 602 for communicating with other systems that are connected to the network 630 (whether illustrated or not) in a distributed environment. Generally, the interface 604 can include, or be implemented using, logic encoded in software or hardware (or a combination of software and hardware) operable to communicate with the network 630. More specifically, the interface 604 can include software supporting one or more communication protocols associated with communications. As such, the network 630 or the interface's hardware can be operable to communicate physical signals within and outside of the illustrated computer 602.

The computer 602 includes a processor 605. Although illustrated as a single processor 605 in FIG. 6, two or more processors 605 can be used according to particular needs, desires, or particular implementations of the computer 602 and the described functionality. Generally, the processor 605 can execute instructions and can manipulate data to perform the operations of the computer 602, including operations using algorithms, methods, functions, processes, flows, and procedures as described in the present disclosure.

The computer 602 also includes a database 606 that can hold data for the computer 602 and other components connected to the network 630 (whether illustrated or not). For example, database 606 can be an in-memory, conventional, or a database storing data consistent with the present disclosure. In some implementations, database 606 can be a combination of two or more different database types (for example, hybrid in-memory and conventional databases) according to particular needs, desires, or particular implementations of the computer 602 and the described functionality. Although illustrated as a single database 606 in FIG. 6, two or more databases (of the same, different, or combination of types) can be used according to particular needs, desires, or particular implementations of the computer 602 and the described functionality. While database 606 is illustrated as an internal component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same, different, or combination of types) can be used according to particular needs, desires, or particular implementations of the computer 602 and the described functionality. While memory 607 is illustrated as an internal component of the computer 602, in alternative implementations, memory 607 can be external to the computer 602.

The application 608 can be an algorithmic software engine providing functionality according to particular needs, desires, or particular implementations of the computer 602 and the described functionality. For example, application 608 can serve as one or more components, modules, or applications. Further, although illustrated as a single application 608, the application 608 can be implemented as multiple applications 608 on the computer 602. In addition, although illustrated as internal to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion and management circuits, including recharging, standby, and power management functionalities. In some implementations, the power-supply 614 can include a power plug to allow the computer 602 to be plugged into a wall socket or a power source to, for example, power the computer 602 or recharge a rechargeable battery.

There can be any number of computers 602 associated with, or external to, a computer system containing computer 602, with each computer 602 communicating over network 630. Further, the terms "client," "user," and other appropriate terminology can be used interchangeably, as appropriate, without departing from the scope of the present disclosure. Moreover, the present disclosure contemplates that many users can use one computer 602 and one user can use multiple computers 602.

Described implementations of the subject matter can include one or more features, alone or in combination.

For example, in a first implementation, a computer-implemented system includes the following. A driver is configured as a driving electromechanical resonator for contacting a drilling fluid in a well. A reference is configured as a reference electromechanical resonator for contacting the drilling fluid in the well. The reference is of a similar construction as the driver and is in contact with the drilling fluid in a substantially same way. A measurement controller is electrically coupled to the driver and the reference and is configured to provide measurement electronics for sensing fluid flow. One or more processors and a non-transitory computer-readable storage medium coupled to the one or more processors store programming instructions for execution by the one or more processors. The programming instructions instruct the one or more processors to perform operations including the following. The driver and the reference are monitored for responses by a measurement controller of a system for measuring fluid flow. The driver is configured as a driving electromechanical resonator for contacting a drilling fluid in a well. The reference is configured as a reference electromechanical resonator for contacting the drilling fluid in the well. The reference is of a similar construction as the driver and is in contact with the drilling fluid in a substantially same way. Real-time measurements are performed by the measurement controller based on information received from the driver and the reference. A viscosity and a density of the drilling fluid are determined by the measurement controller based on the real-time measurements and the similar construction. The similar construction of the driver and the reference enables the measurement controller to mitigate environmental sensitivities of the driver and the reference and to enhance fluid property sensitivities by the driver and the reference to physical properties of the drilling fluid.

The foregoing and other described implementations can each, optionally, include one or more of the following features:

A first feature, combinable with any of the following features, where the driver faces the reference so that acoustic pulses travel directly between the driver and the reference.

A second feature, combinable with any of the previous or following features, the system further including a reflector configured to reflect acoustic pulses, where the driver and the reference face the reflector so that acoustic pulses travel between the driver and the reference by bouncing from the reflector.

A third feature, combinable with any of the previous or following features, where the driver and the reference reside on a common plane.

A fourth feature, combinable with any of the previous or following features, where the operations further including: capturing, by the measurement controller, fluid velocity information for the drilling fluid; and normalizing, by the measurement controller, viscosity measurements in nonlinear, velocity-dependent viscosity drilling fluids.

A fifth feature, combinable with any of the previous or following features, the operations further including modeling behavior of the driving electromechanical resonator and the reference electromechanical resonator using a Butterworth Van Dyke equivalent circuit.

A sixth feature, combinable with any of the previous or following features, where the driver and the reference are displaced on a same side of a fixed geometry.

In a second implementation, a computer-implemented method includes the following. A driver and a reference are monitored for responses by a measurement controller of a system for measuring fluid flow. The driver is configured as a driving electromechanical resonator for contacting a drilling fluid in a well. The reference is configured as a reference electromechanical resonator for contacting the drilling fluid in the well. The reference is of a similar construction as the driver and is in contact with the drilling fluid in a substantially same way. Real-time measurements are performed by the measurement controller based on information received from the driver and the reference. A viscosity and a density of the drilling fluid are determined by the measurement controller based on the real-time measurements and the similar construction. The similar construction of the driver and the reference enables the measurement controller to mitigate environmental sensitivities of the driver and the reference and to enhance fluid property sensitivities by the driver and the reference to physical properties of the drilling fluid.

The foregoing and other described implementations can each, optionally, include one or more of the following features:

A first feature, combinable with any of the previous or following features, the driver faces the reference so that acoustic pulses travel directly between the driver and the reference.

A second feature, combinable with any of the previous or following features, the method further including reflecting, by a reflector, acoustic pulses, where the driver and the reference face the reflector so that acoustic pulses travel between the driver and the reference by bouncing from the reflector.

A third feature, combinable with any of the previous or following features, where the driver and the reference reside on a common plane.

A fourth feature, combinable with any of the previous or following features, the method further including: capturing, by the measurement controller, fluid velocity information for the drilling fluid; and normalizing, by the measurement controller, viscosity measurements in nonlinear, velocity-dependent viscosity drilling fluids.

A fifth feature, combinable with any of the previous or following features, the method further including modeling behavior of the driving electromechanical resonator and the reference electromechanical resonator using a Butterworth Van Dyke equivalent circuit.

A sixth feature, combinable with any of the previous or following features, where the driver and the reference are displaced on a same side of a fixed geometry.

In a third implementation, a non-transitory, computer-readable medium stores one or more instructions executable by a computer system to perform operations including the following. A driver and a reference are monitored for responses by a measurement controller of a system for measuring fluid flow. The driver is configured as a driving electromechanical resonator for contacting a drilling fluid in a well. The reference is configured as a reference electromechanical resonator for contacting the drilling fluid in the well. The reference is of a similar construction as the driver and is in contact with the drilling fluid in a substantially same way. Real-time measurements are performed by the measurement controller based on information received from the driver and the reference. A viscosity and a density of the drilling fluid are determined by the measurement controller based on the real-time measurements and the similar construction. The similar construction of the driver and the reference enables the measurement controller to mitigate environmental sensitivities of the driver and the reference and to enhance fluid property sensitivities by the driver and the reference to physical properties of the drilling fluid.

The foregoing and other described implementations can each, optionally, include one or more of the following features:

A first feature, combinable with any of the previous or following features, the driver faces the reference so that acoustic pulses travel directly between the driver and the reference.

A second feature, combinable with any of the previous or following features, the operations further including reflecting, by a reflector, acoustic pulses, where the driver and the reference face the reflector so that acoustic pulses travel between the driver and the reference by bouncing from the reflector.

A third feature, combinable with any of the previous or following features, where the driver and the reference reside on a common plane.

A fourth feature, combinable with any of the previous or following features, the operations further including: capturing, by the measurement controller, fluid velocity information for the drilling fluid; and normalizing, by the measurement controller, viscosity measurements in nonlinear, velocity-dependent viscosity drilling fluids.

A fifth feature, combinable with any of the previous or following features, the operations further including modeling behavior of the driving electromechanical resonator and the reference electromechanical resonator using a Butterworth Van Dyke equivalent circuit.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/–R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented system for measuring fluid flow, comprising:
   a driver configured as a driving electromechanical resonator for contacting a drilling fluid in a well;
   a reference configured as a reference electromechanical resonator for contacting the drilling fluid in the well, wherein the reference is of a similar construction as the driver and is in contact with the drilling fluid in a substantially same way;
   a measurement controller electrically coupled to the driver and the reference and configured to provide measurement electronics for sensing fluid flow;
   one or more processors; and
   a non-transitory computer-readable storage medium coupled to the one or more processors and storing programming instructions for execution by the one or more processors, the programming instructions instructing the one or more processors to perform operations comprising:
monitoring, by the measurement controller based on the similar construction of the driver and the reference, responses from the driver and the reference to mitigate environmental sensitivities of the driver and the reference and to enhance fluid property sensitivities by the driver and the reference to physical properties of the drilling fluid;
performing, by the measurement controller, real-time measurements based on information received from the driver and the reference; and
determining, by the measurement controller based on the real-time measurements, a viscosity and a density of the drilling fluid.

2. The computer-implemented system of claim 1, wherein the driver faces the reference so that acoustic pulses travel directly between the driver and the reference.

3. The computer-implemented system of claim 1, the operations further comprising:
capturing, by the measurement controller, fluid velocity information for the drilling fluid; and
normalizing, by the measurement controller, viscosity measurements in nonlinear, velocity-dependent viscosity drilling fluids.

4. The computer-implemented system of claim 1, the operations further comprising modeling behavior of the driving electromechanical resonator and the reference electromechanical resonator using a Butterworth Van Dyke equivalent circuit.

5. The computer-implemented system of claim 1, wherein the driver and the reference are displaced on a same side of a fixed geometry.

6. The computer-implemented system of claim 1, further comprising a reflector configured to reflect acoustic pulses, wherein the driver and the reference face the reflector so that acoustic pulses travel between the driver and the reference by bouncing from the reflector.

7. The computer-implemented system of claim 6, wherein the driver and the reference reside on a common plane.

8. A computer-implemented method, comprising:
monitoring, by a measurement controller of a system for measuring fluid flow, responses from: i) a driver configured as a driving electromechanical resonator for contacting a drilling fluid in a well, and ii) a reference configured as a reference electromechanical resonator for contacting the drilling fluid in the well, wherein the reference is of a similar construction as the driver and is in contact with the drilling fluid in a substantially same way;
performing, by the measurement controller, real-time measurements based on information received from the driver and the reference; and
determining, by the measurement controller based on the real-time measurements and the similar construction, a viscosity and a density of the drilling fluid, wherein similar construction of the driver and the reference enables the measurement controller to mitigate environmental sensitivities of the driver and the reference and to enhance fluid property sensitivities by the driver and the reference to physical properties of the drilling fluid.

9. The computer-implemented method of claim 8, wherein the driver faces the reference so that acoustic pulses travel directly between the driver and the reference.

10. The computer-implemented method of claim 8, further comprising:
capturing, by the measurement controller, fluid velocity information for the drilling fluid; and
normalizing, by the measurement controller, viscosity measurements in nonlinear, velocity-dependent viscosity drilling fluids.

11. The computer-implemented method of claim 8, further comprising modeling behavior of the driving electromechanical resonator and the reference electromechanical resonator using a Butterworth Van Dyke equivalent circuit.

12. The computer-implemented method of claim 8, wherein the driver and the reference are displaced on a same side of a fixed geometry.

13. The computer-implemented method of claim 8, further comprising:
reflecting, by a reflector, acoustic pulses, wherein the driver and the reference face the reflector so that acoustic pulses travel between the driver and the reference by bouncing from the reflector.

14. The computer-implemented method of claim 13, wherein the driver and the reference reside on a common plane.

15. A non-transitory, computer-readable medium storing one or more instructions executable by a computer system to perform operations comprising:
monitoring, by a measurement controller of a system for measuring fluid flow, responses from: i) a driver configured as a driving electromechanical resonator for contacting a drilling fluid in a well, and ii) a reference configured as a reference electromechanical resonator for contacting the drilling fluid in the well, wherein the reference is of a similar construction as the driver and is in contact with the drilling fluid in a substantially same way;
performing, by the measurement controller, real-time measurements based on information received from the driver and the reference; and
determining, by the measurement controller based on the real-time measurements and the similar construction, a viscosity and a density of the drilling fluid, wherein similar construction of the driver and the reference enables the measurement controller to mitigate environmental sensitivities of the driver and the reference and to enhance fluid property sensitivities by the driver and the reference to physical properties of the drilling fluid.

16. The non-transitory, computer-readable medium of claim 15, wherein the driver faces the reference so that acoustic pulses travel directly between the driver and the reference.

17. The non-transitory, computer-readable medium of claim 15, the operations further comprising:
capturing, by the measurement controller, fluid velocity information for the drilling fluid; and
normalizing, by the measurement controller, viscosity measurements in nonlinear, velocity-dependent viscosity drilling fluids.

18. The non-transitory, computer-readable medium of claim 15, the operations further comprising modeling behavior of the driving electromechanical resonator and the reference electromechanical resonator using a Butterworth Van Dyke equivalent circuit.

19. The non-transitory, computer-readable medium of claim 15, the operations further comprising:
reflecting, by a reflector, acoustic pulses, wherein the driver and the reference face the reflector so that acoustic pulses travel between the driver and the reference by bouncing from the reflector.

20. The non-transitory, computer-readable medium of claim 19, wherein the driver and the reference reside on a common plane.

\* \* \* \* \*